(12) United States Patent
Henning et al.

(10) Patent No.: US 6,261,440 B1
(45) Date of Patent: *Jul. 17, 2001

(54) INTERFERENCE FREE BIOSENSOR (75) Inventors: Timothy P. Henning, Vernon Hills; Thomas G. Spring, Highland Park, both of IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 08/928,364

(22) Filed: Sep. 12, 1997

Related U.S. Application Data (63) Continuation-in-part of application No. 08/563,728, filed on Dec. 18, 1995, now Pat. No. 5,755,953.

(51) Int. Cl.[7] .......................................... G01F 1/64

(52) U.S. Cl. ...................... 205/792; 204/403; 265/777.5; 265/780; 265/782; 265/794.5; 435/817

(58) Field of Search .......................... 204/403; 205/777.5, 205/780, 782, 794.5; 435/817

(56) References Cited

U.S. PATENT DOCUMENTS

| | | | |
|---|---|---|---|
| 5,173,165 | * 12/1992 | Schmid et al. | 204/403 |
| 5,202,261 | * 4/1993 | Musho et al. | 204/403 |
| 5,225,064 | 7/1993 | Henkens et al. | |
| 5,273,896 | 12/1993 | Pedersen et al. | |
| 5,700,770 | * 12/1997 | Damhus et al. | 510/305 |
| 5,755,953 | * 5/1998 | Henning et al. | 205/778 |

FOREIGN PATENT DOCUMENTS

| | | |
|---|---|---|
| 0078990 | 5/1983 | (EP) . |
| 2276724 | 10/1994 | (GB) . |
| 9323748 | 11/1993 | (WO) . |
| 9606947 | 3/1996 | (WO) . |
| 9722715 | 6/1997 | (WO) . |

OTHER PUBLICATIONS

Wang et al. ("Metal–Dispersed Carbon Paste Electrodes", Anal. Chem. month unknown 1992, 64, 1285–188).*

Johansson et al. ("A reagentless amperometric biosensr for alcohol detection in column liquid chromatography based on co–immobilized peroxidase and alcohol oxidase in carbon paste", Journal of Biotechnology, 31 (month unknown 1993) 301–316).*

Kacaniklic et al. ("Amperometric Biosensors for Detection of L–and D–Amino Acids Based on Coimmobilized Peroxidase and L– and D–Amino Acid Oxidases in Carbon Paste Electrodes", Electroanalysis, 6(month unknown 1994) 391–390).*

E. Csöregi, et al., "Carbon fibres as electrode materials for the construction of peroxidase–modified amperometric biosensors.", Analytica Chimica Acta, vol. 273, No. 1–2, 1993, pp. 59–70.

G. Jönsson–Pettersson, "Reagentless hydrogen peroxide and glucose sensors based on peroxidase immobilized on graphite electrodes.", Electroanalysis, vol. 3, No. 8, Oct. 1991, pp. 741–750.

Marko–Varga, et al., Enzyme–based biosensor as a selective detection unit in column liquid chromatography, Journal of Chromatography A, 660 (1994) pp 153–167 month unknown.

(List continued on next page.)

*Primary Examiner*—T. Tung
*Assistant Examiner*—Alex Noguerola
(74) *Attorney, Agent, or Firm*—David L. Weinstein (57) ABSTRACT

Provided are microparticle forms of carbon, carbon catalysts and carbon-containing electrically conductive materials which are covalently linked to peroxidase. The carbon:peroxidase conjugates are suitable for use as substrates in conventional electrodes. Surprisingly, the conjugates display very little sensitivity to known interfering substances and thus are suitable for use as interference free electrodes.

17 Claims, 3 Drawing Sheets

OTHER PUBLICATIONS

Cardosi, Hydrogen Peroxide–Sensitive Electrode Based on Horseradish Perioxidase–Modified Platinized Carbon, Electroanalysis 6 (1994) pp 89–96 month unknown.

Cardosi, et al.,Screen printed glucose electrodes based on platinised carbon particles and glucose oxidase, Analytica Chimica Acta, 276 (1993) pp 69–74 month unknown.

Cardosi et al. ("Screen printed glucose electrodes based on platinized carbon particles and glucose oxidase", Analytica chimica Acta, 276(month unknown 1993) 69–74).*

Marko–Varga et al. ("Enzyme–based biosensor as a selective dection unit in column liquid chromatography", J. Chromatography A, 660 (month unknown 1994) 153–167).*

Cardosi et al. ("Hydrogen peroxide–sensitive electrode based on Horseradish peroxidase–modified platinized carbon", electroanalysis, 6 (month unknown 1994) 89–96).*

* cited by examiner-

INTERFERENCE FREE BIOSENSOR

This application is a continuation-in-part of U.S. Ser. No. 08/563,728, filed Dec. 18, 1995, now U.S. Pat. No. 5,755, 953.

FIELD OF THE INVENTION

The present disclosure is in the field of biosensors for the analysis of body fluids.

BACKGROUND OF THE INVENTION

One method for measuring the concentration of glucose in blood is to cause a reaction between the glucose and the enzyme glucose oxidase. The reaction produces hydrogen peroxide, which can be electrochemically oxidized at positive potentials. The current produced by the oxidation of peroxide is measured and is proportional to the glucose concentration in the blood. A similar scheme may be used to measure other analytes of interest by selecting the appropriate enzyme that will produce hydrogen peroxide in proportion to the concentration of the analyte, e.g., lactate may be similarly measured using the enzyme lactate oxidase.

A long standing problem with these measurement techniques is that of interference from other substances. Blood may contain other components which can oxidize at the same potential as hydrogen peroxide; prevalent among these are urate and acetaminophen. As these or other interfering substances oxidize, the current resulting from their oxidation is added to and indistinguishable from the current resulting from the oxidation of the hydrogen peroxide. An error therefore results in the quantification of the peroxide and consequently the blood analyte.

Many methods have been tried to reduce or eliminate these interferences. Acetaminophen has been particularly difficult to eliminate because, unlike urate, acetaminophen is not charged. One methodology disclosed in the art (see, e.g., Sittampalam, G., and Wilson, G. S., Analytical Chemistry, 55:1608–1610, 1983, and Geise, R. J., et al, Biosensors and Bioelectronics, 6:151–160, 1991) has been to use one or more selectively permeable membranes to prevent the interfering substances from contacting the electrode, although this method is not effective at fully preventing interference.

An alternate method for preventing interference is disclosed in U.S. Pat. Nos. 5,225,064 and 5,334,296. This method decreases the electrical potential of the reaction to a state where urate and acetaminophen are not oxidized. This may be accomplished by employing an enzyme that will reduce hydrogen peroxide, such as a form of peroxidase, in the electrode. In this type of system, the hydrogen peroxide reacts with the peroxidase, in which reaction the hydrogen peroxide is reduced and the peroxidase oxidizes. If the peroxidase is in intimate contact with an electrode's surface, the peroxidase can be reduced at the electrode by imposing an electrical potential. The magnitude of the current required to reduce the peroxidase is proportional to the concentration of the hydrogen peroxide and hence proportional to the concentration of glucose or other analyte of interest. Moreover, the reactions occur at potentials at which urate and acetaminophen do not oxidize and therefore do not interfere.

The art recognizes the use of horseradish peroxidase or fungal peroxidase physically adsorbed to a gold or carbon surface in attempts to prevent interference (see, e.g., U.S. Pat. Nos. 5,225,064 and 5,334,296; Ho, W. O., et al, J. Electroanal. Chem., 351:187–197, 1993; Wollenberger, U., et al, Bioelectrochemistry and Bioenergetics, 26:287–296, 1991; Csoregi, E., et al, Anal. Chem. 66:3604–3610, 1994). However these reports indicate that such use has yielded unsatisfactory results as the magnitude of the electric currents forming the signals in these applications are quite small and the linearity is poor at high peroxide concentrations.

There is great utility, therefore, in the development of an electrode system in which hydrogen peroxide reacts in a measurable way, generating signal currents of usable magnitudes and that are linear to high concentrations, yet which are not subject to interference caused by the oxidation of interfering substances such as urate and acetaminophen.

SUMMARY OF THE INVENTION

The present disclosure provides microparticle carbon covalently linked to peroxidase. Preferably, the microparticle carbon is native microparticle carbon conjugated to microperoxidase via a bifunctional reagent.

The present disclosure also provides microparticle carbon:peroxidase conjugates useful as an electrode for the determination of an analyte in a sample. The preferred electrode comprises native microparticle carbon covalently linked to microperoxidase in a resin matrix.

DETAILED DESCRIPTION OF THE INVENTION

Embodiments of the invention generally comprise an electrode used to electrochemically measure the concentration of an analyte of interest in a solution. The biosensor or electrode includes a peroxidase enzyme covalently bound to microparticle carbon and retained in a matrix in intimate contact with the electrode.

As used herein, the term "microparticle carbon" refers to fine particles of carbon, carbon catalysts (e.g., platinized carbon, ruthenium containing carbon, etc.) and carbon-containing conductive compounds (e.g., polypyrrole, polyaniline). Microparticle carbon in a variety of forms are known in the art and may be readily obtained from commercial vendors. For ease of use and handling, it is preferred that the microparticle carbon be less than 1000 nanometers (1 micron) in diameter, preferably in the range of 5–50 nm. In the experiments described below, a fine (30 nm) particle carbon (Vulcan XC72R; E-TEk, Natick Mass.) is used.

The microparticle carbon can be used in its native state ("native") or various functional groups can be attached to the carbon ("derivatized") following techniques known in the art. For derivatized carbon, the carbon microparticle is reacted with a bifunctional reagent, preferably with a bifunctional agent having amine-containing function groups. As bifunctional reagents are available having a wide variety linkers of differing lengths between the two functional ends, one can easily and rapidly determine those reagents which are suitable for use with a variety of enzymes and for a variety of applications. The resulting derivatized carbon particles can be immediately coupled to the enzyme or can be stored prior to enzyme coupling.

The derivatized or native particles are covalently attached to the enzyme, again following techniques known in the art, and as described in more detail below.

Peroxidase of any origin is useful in the interference free biosensor of the invention. Peroxidase is readily obtained following techniques known in the art, or alternatively, may be purchased from commercial vendors. In a preferred embodiment, the peroxidase is microperoxidase such as described European Patent Publication 0 195 320.

As microparticle carbon with attached enzyme cannot by itself be readily used for the detection of an analyte of interest, the carbon should be physically confined in such a manner that the analyte may be brought into contact with the carbon:enzyme conjugate. Any of the confinement means known in the art of e.g., gold:peroxidase conjugates, are suitable for use in the present invention as well. For example, by the use of semi- or selectively-permeable membranes, the carbon can be physically restrained while allowing the analyte of interest to come into intimate contact with the peroxidase enzyme. In a preferred embodiment, the microparticle carbon:enzyme conjugate is used for construction of an electrode. In this particular embodiment, the microparticle carbon:enzyme conjugate is confined to an electrically conductive surface in order to form an electrode. Of the many ways of confining the carbon:enzyme microparticle to a surface which are known in the art, the procedure described in International Patent Publication WO 95/22057 is preferred. The method described therein incorporates the particles into a resin matrix (also referred to as "paint") and has the benefits of being water based to preserve enzyme activity. It also yields a liquid, facilitating dispensing and easing the manufacturing of electrodes. As disclosed therein, the liquid resin with the contained carbon particles dries to form a water insoluble film which is compatible with blood.

The enzyme:microparticle carbon of the invention is useful in any application where the catalytic properties of peroxidase prove beneficial. Significantly, the enzyme:microparticle carbon of the invention provides a composition which is essentially free of interference from compounds which normally interfere with peroxide determinations. Thus the enzyme:microparticle carbon of the invention can be used in instrument based systems (in vitro) or in devices for the direct measurement of blood analytes in vivo.

EXAMPLE 1

Covalent Coupling of Microperoxidase to Carbon Particles

In this experiment, native and two forms of derivatized carbon particles are covalently coupled to microperoxidase.

The first form of derivatized carbon utilizes the functional group ethylenediamine (Aldrich, Milwaukee Wis.) attached to carbon by mixing 100 mg of carbon with 27 mg of ethylenediamine in 5 mL of a 50 mM 2[N-Morpholino]-ethanesulfonic Acid (MES) (Sigma, St. Louis Mo.) buffer at pH 5.5. 50 mg of 1-(3-Dimethylaminopropyl)-3-ethylcarbodiimide hydrochloride (EDC) (Pierce, Rockford Ill.) is then added to initiate the coupling and allowed to react for 1 hour. The derivatized carbon is removed by centrifugation and washed three times with water.

In a second form of derivatized carbon, a poly (oxyalkylene)diamine (JEFFAMINE® ED-600; Texaco, Houston Tex.) is employed as the functional reagent and is attached to carbon by mixing 100 mg of carbon with 240 mg of the diamine in 5 mL of a 4% pyridine/water solution at pH 5.5. 4 mg of EDC is then added to initiate the coupling and allowed to react overnight. The derivatized carbon is then removed by centrifugation and washed three times with water.

The peroxidase enzyme is covalently coupled to the native or derivatized microparticle carbon using EDC. 100 mg of carbon is mixed with 20 mg of the peroxidase enzyme (for example, MP-11 microperoxidase from Sigma Chemical, St. Louis, Mo.) in 5 mL of a 50 mM MES buffer, pH 5.5. Alternatively, and preferably, the buffer can be 4% pyridine/water solution at pH 5.5. 10 mg of EDC is added and the solution is mixed for 1 hour. The carbon with covalently attached peroxidase enzyme is removed by centrifugation and washed with water. The carbon with attached enzyme is stored wet.

To provide a comparison to covalent coupling, enzyme adsorption is done in a solution of 50 mM sodium phosphate, 1 mM EDTA, 100 mM sodium chloride, and 0.05% antimicrobial (Kathon CG; Rohm and Haas, Philadelphia Pa.) solution at a pH of 7.5. This solution is referred to as PESK 7.5. 125 mg of carbon is mixed with 25 mg of the enzyme in 5 mL of PESK 7.5 overnight. The carbon is then removed by centrifugation and washed three times with PESK 7.5.

EXAMPLE 2

Preparation of the Paint

A resin matrix for retaining the carbon on a conductive surface, termed F133 Resin, is made by combining the following weights of each component:

| | |
|---|---:|
| Joncryl 537 (Johnson Wax, Racine WI) | 65.04 mg |
| NH$_4$OH, 10% in water | 8.91 mg |
| 2-Ethoxy-ethanol (Aldrich, Milwaukee WI) | 20.94 mg |
| Dibutyl Phthalate (Fluka, Ronkonkoma, NY) | 7.13 mg |
| Surfynol 104H (Air Products, Allentown, PA) | 2.50 mg |
| Surfynol 695 (Air Products) | 5.0 mg |
| Acrysol 275 (Rohm and Haas, Philadelphia, PA) | 30.6 mg |

72 mg of the resin, a liquid, is then combined with 160 mg of the carbon:enzyme conjugate compacted in the wet state, 262 mg of 0.085 M trehalose (Sigma, St. Louis, Mo.) in water. A vigorous mixing of the three components is done using an amalgamator (WIG-L-BUG; Crescent Dental Co., Lyons Ill.) for 3 minutes, forming a liquid suspension. This suspension or paint may then be applied to an electrode.

EXAMPLE 3

Electrode Construction

Figure 1:
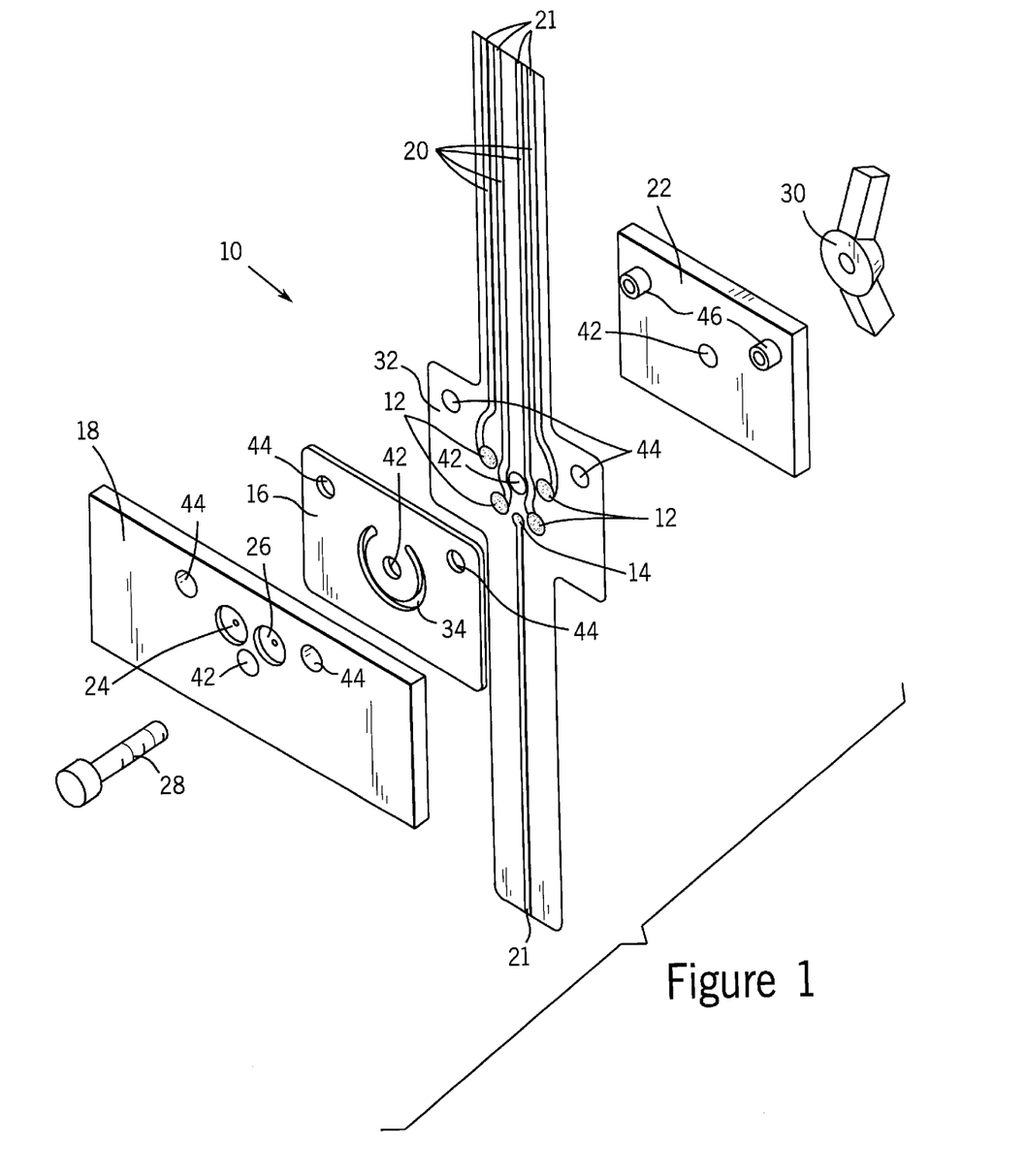
FIG. 1 shows an analytical electrode embodying the interference free biosensor of the invention.

The carbon:enzyme conjugates are utilized in an analytical electrode of the type described in International Patent Publication WO 95/22057. Briefly, an analytical electrode assembly for testing the carbon:enzyme conjugates of the invention is shown in FIG. 1. Electrode assembly 10 consists of one or more (in this figure, four) biosensors 12 mounted on a polyester sheet 32. The biosensors 12 are constructed by printing silver/silver chloride (Acheson SS24540) electrical connections 20 on the polyester sheet 32. At the location for electrical contact with the instrument 21 as well as the terminus of the electrical connection 20, an electrically conducting trace is formed by screen printing of carbon ink (Acheson 423SS) over the electrical connection 20. The carbon surface is masked by the application of a screen printed dielectric (Acheson ML 25208), leaving 0.013 cm² of carbon exposed for application of the paint at 12. 0.2 to 1.0 µl of carbon:enzyme conjugate paint is applied to the exposed surface of the carbon trace using a hand dispenser. Reference electrode 14 is printed using silver/silver chloride (Acheson SS24540). An additional counter electrode (not visible in FIG. 1) is formed on face plate 18 on the side facing gasket 16. The counter electrode is printed with carbon as described above, however no paint is applied. Gasket 16 provides a flow channel 34 when sandwiched between polyester sheet 32 and front plate 18. Fluid may then flow over the biosensors 12, reference electrode 14, and the counter electrode (not shown) from entry port 24 exiting via exit port 26. Back plate 22 may be fastened to front plate 18 via a fastening means such as a nut 28 inserted through fastening hole 42 to bolt 30. Optionally, alignments means may be provided to ensure proper registry of the components via holes 44 and pins 46.

EXAMPLE 4

Demonstration of Sensitivity a. Several electrodes are fabricated as described in Examples 1 through 3, utilizing different enzymes (horseradish peroxidase, soybean peroxidase, and microperoxidase), different carbon attachment methods (adsorption or covalent coupling), and different carbon treatments (native, ethylenediamine, or JEFFAMINE ED-600). A test solution of about 0.1 mM hydrogen peroxide at 37° C. is passed over the carbon trace, the reference electrode, and the counter electrode. A fixed electrical potential of 100 mV is applied to the electrode, and the resulting electrical current is recorded for various electrode types using a standard three electrode circuit. The measured currents for various combinations of enzyme, carbon attachment technique, and carbon treatment are as follows:

| Enzyme | Carbon Attachment | Carbon Treatment | Current (nA) |
| --- | --- | --- | --- |
| Horseradish Peroxidase | Adsorption | None | −34 |
| Horseradish Peroxidase | Covalent | Ethylene-diamine | −187 |
| Horseradish Peroxidase | Covalent | JEFFAMINE | −324 |
| Soybean Peroxidase | Covalent | Ethylene-diamine | −407 |
| Soybean Peroxidase | Covalent | JEFFAMINE | −442 |
| Microperoxidase | Adsorption | None | −46 |
| Microperoxidase | Covalent | None | −1023 |

As apparent from the foregoing, covalently attached microperoxidase shows much larger currents than the conventional method of adsorption. Covalently attached microperoxidase (MP-11, Sigma, St. Louis Mo.) yields much larger currents than other peroxidase enzymes such as horseradish peroxidase (Type II, Sigma) and soybean peroxidase (Enzymol International, Inc., Bexley Ohio).

b. Potassium ferricyanide also reduces in a reversible reaction that is similar to peroxidase. It is well recognized in the art, see, e.g., Csoregi, E., et al, that when equal concentrations of peroxide and ferricyanide are employed, the current produced from the peroxidase is 30–60 X less than the current produced from the ferricyanide. To assess the sensitivity of the present invention, the current resulting from the reduction of peroxide at the present electrodes is compared to the current resulting from the reduction of potassium ferricyanide. Hydrogen peroxide and ferricyanide at substantially equal concentrations of about 0.05 mM at about 37° C. are passed over an embodiment of the electrode described here having microperoxidase covalently coupled to native carbon. Surprisingly, the current for peroxide reduction was twice that as for ferricyanide reduction (see following table).

| Analyte | Applied Potential (mV) | Current (nA) |
| --- | --- | --- |
| Hydrogen Peroxide | 100 | −147 |
| Ferricyanide | 0 | −70 |

Because the peroxide reduction involves two electrons as opposed to one for ferricyanide, a signal produced by the present invention which is twice that produced by ferricyanide indicates extremely fast electron transfer from the carbon to the microperoxidase enzyme (at least as fast as that for the reversible Ferri/Ferrocyanide reaction). This has never been achieved before, and demonstrates the sensitivity of the invention.

EXAMPLE 5

Demonstration of Linearity

Electrodes are made with soybean and horseradish peroxidase covalently coupled to ethylenediamine derivatized carbon and microperoxidase covalently coupled to native carbon. The response of the electrodes to varying levels of hydrogen peroxide at about 37° C. and an electrode potential of 100 mV is measured, with the following results.

| Enzyme | Current (nA) 0.005 mM $H_2O_2$ | Current (nA) 0.010 mM $H_2O_2$ | Current (nA) 0.100 mM $H_2O_2$ | Current (nA) 0.300 mM $H_2O_2$ |
| --- | --- | --- | --- | --- |
| Soybean Peroxidase | −70 | −114 | −407 | — |
| Horseradish Peroxidase | −69 | −102 | −257 | — |
| Microperoxidase | −13 | −27 | −237 | −669 |

As can be seen, neither soybean nor horseradish peroxidase are linear over the range tested. Readings at higher concentrations are not taken as the response is significantly diminished and thus the information is not informative. On the other hand, microperoxidase demonstrates linearity to at least 0.3 mM hydrogen peroxide.

In the literature to date, horseradish or fungal peroxidase have been favored over microperoxidase for use in the detection of peroxide. However, embodiments of this invention utilizing microperoxidase far exceed applications with other peroxidase enzymes in not only signal size but also in linearity.

EXAMPLE 6

Measurement of Glucose Concentrations

In this example, glucose is measured using a commercial instrument (Nova Biomedical Stat Profile 10) in which the paint of the present invention is used in commercial electrodes supplied by the manufacturer.

Microperoxidase is covalently attached to native carbon as described in Examples 1 and a paint is made as described in Example 2. The paint is applied to the center of the interior surface of a Nova Biomedical glucose enzyme cap in such a way that the paint is aligned with the platinum working electrode of the electrode body. The paint is allowed to dry and the cap is then placed on the glucose electrode body. The control electrode is an unmodified glucose electrode, i.e., as supplied by the manufacturer, and is operated in accordance with the manufacturer's instructions. The modified electrode is placed in a flow cell and glucose solutions having varying levels of interfering substances are passed over the electrode, with flow stopped for measurements. The current is measured using a potentiostat, with about 100 mV potential applied. The glucose level is kept constant at about 2 mM at a temperature of about 37° C. to simulate a hypoglycemic diabetic sample. Acetaminophen is varied up to the toxic limit of 2 mM. The percentage change in signal of the electrode in the absence and presence of acetaminophen is quantified, with the results shown in FIG. 2.

Figure 2:
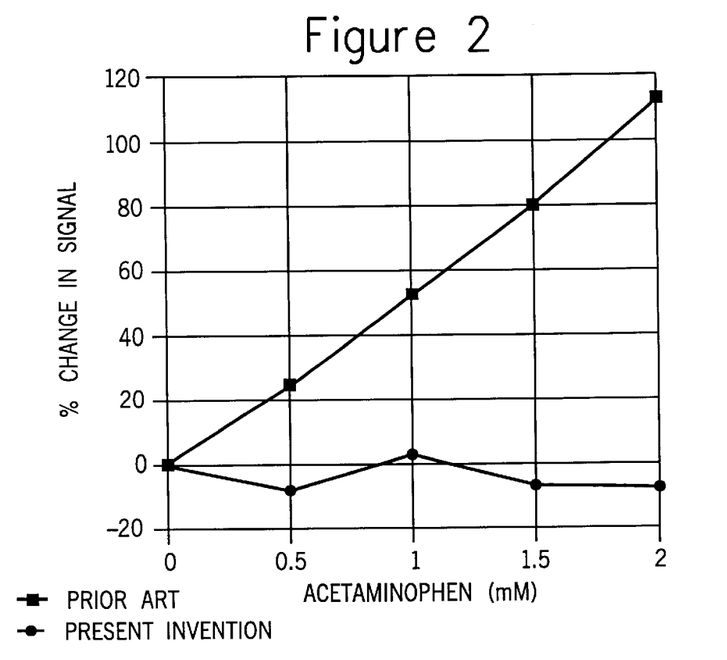
FIG. 2 is a graph illustrating % change in glucose signal vs. acetaminophen concentration in a 2 mM glucose solution.

The results indicate that there is essentially no effect of acetaminophen on the glucose measurement of the electrode embodiment described here.

EXAMPLE 7

Measurement of Lactate Concentration

Figure 3:
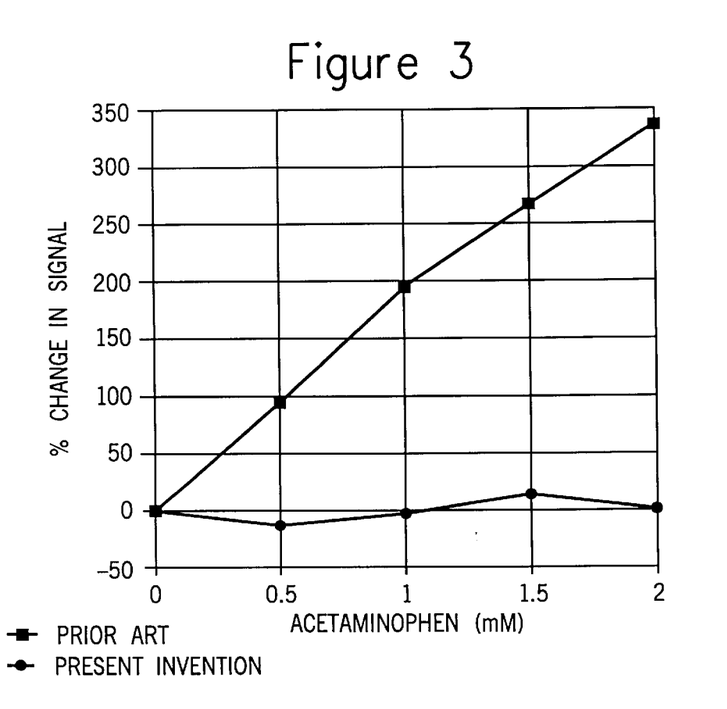
FIG. 3 is a graph illustrating % change in lactate signal vs. acetaminophen concentration in a 3 mM lactate solution.

An experiment similar to that of Example 6 is conducted using a Nova Biomedical Lactate enzyme cap. As lactate is found in lower concentrations in blood than glucose, a 0.3 mM lactate solution is used. Again, as shown in FIG. 3, the utilization of the microperoxidase of the present invention eliminates interference due to acetaminophen on lactate measurement.

EXAMPLE 8

Comparison of Microperoxidase to Porphyrins

It is known in the art that porphyrin can act as a catalyst. Because microperoxidase is essentially a short peptide chain of 11 amino acids which is covalently attached to a porphyrin ring, and thus many similarities exist in chemical structure between porphyrins and microperoxidase, the following experiment assesses the necessity of the peptide chain in the catalytic reduction of peroxide.

Cobalt is inserted into Protoporphyrin IX dimethylester (Sigma) with the following procedure. 50 mg of porphyrin is dissolved in 25 mL of DMF in a 100 mL round bottomed flask. 50 mg of the cobalt chloride (Sigma) is added and refluxed until the florescence is quenched. The solution is then cooled and cold water is added to recrystalize the cobalt porphyrin. After washing and drying, cobalt porphyrin is adsorbed to 250 mg of wet carbon. The adsorption is done by mixing 10 mg of dry porphyrin with carbon in 5 mL of chloroform. After removing chloroform by washing with acetone and water, the cobalt porphyrin is made into a paint by mixing about 160 mg of carbon:adsorbed porphyrin, 72 mg of F133 resin, and 262 mg of 0.085 M trehalose in water. The paint is dispensed on the screen printed electrode described in Example 3. The reduction of 0.1 mM hydrogen peroxide is recorded for cobalt porphyrin electrodes and microperoxidase (covalently linked to native carbon) electrodes at different potentials. The results are set forth in FIG. 4.

Figure 4:
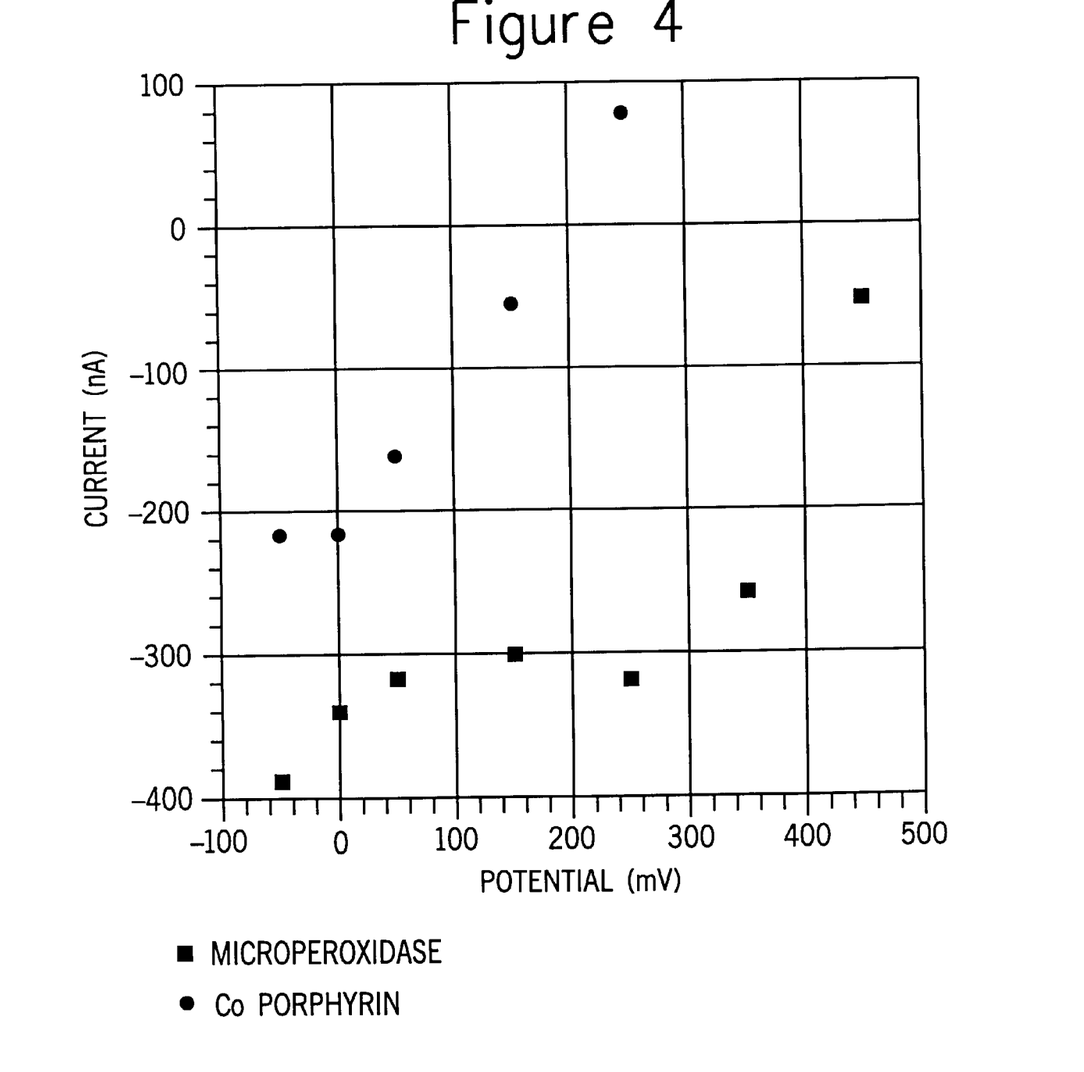
FIG. 4 is a graph illustrating reduction of 0.1 mM hydrogen peroxide as a function of potential.

These results show that a microperoxidase containing paint of the present invention is capable of reducing peroxide at potentials approximately 400 mV more easily than cobalt porphyrin. This indicates that microperoxidase performs significantly better than porphyrin in the catalytic reduction of peroxide.

EXAMPLE 9

Synthesis of Alternate Microperoxidase Enzymes

The following experiment is designed to explore the necessity of iron to the catalytic property of microperoxidase. The results indicate that the metal moiety is necessary for catalytic activity, and, surprisingly, activity is retained when the native iron is removed and replaced with other metals.

a. Iron is removed from microperoxidase by adding 800 mg of iron sulfate in 4 mL of concentrated HCl to 2000 mg of enzyme dissolved in 14 mL of glacial acetic acid. This reaction mixture is left stirring under nitrogen for 10 minutes during which the maroon color of the solution turned purple. Acetone is added to the solution until the microperoxidase precipitates. This solid is then collected, washed by centrifugation with acetone, and dried.

b. To insert the various metals, 20 mg of the microperoxidase from Example 9a (referred to hereafter as "deironated" peroxidase) is dissolved in 4 mL of a 1:3 pyridine:acetic acid solution. The solution is heated to 80° C. under nitrogen and 20 mg of metal (e.g., iron, zinc, copper, nickel) in the form of the sulfate or chloride salt, is added in 1 mL of water. The mixture is reacted under nitrogen at 80° C. for 10 min. followed by cooling in air for 10 min. Acetone is added to precipitate the microperoxidase, and the solids are washed with acetone.

Each microperoxidase containing a different metal is tested for activity prior to covalent coupling to carbon. The activity is measured by observing the rate of formation of the quinoneimine dye from 4-aminoantipyrine and 2-hydroxy-3,5-dichlorobenzene sulfonic acid at 550 nm in the presence of an excess of hydrogen peroxide. The following relative activity results are determined.

| Microperoxidase | Activity ($\mu$g/mL) |
| --- | --- |
| Untreated | 3.79 |
| "De-ironated" | 0.008 |
| Iron | 2.848 |
| Zinc | 1.694 |
| Copper | 0.128 |
| Nickel | 1.78 |

The results indicate an approximately 25% loss in activity following removal and replacement of iron. The zinc and nickel microperoxidases show approximately a 50% loss in activity. Copper microperoxidase is not very active.

The microperoxidase enzymes containing different metal ions are covalently coupled to native carbon using the procedure described in Example 1. Paints are prepared using about 160 mg of carbon:enzyme conjugate, 72 mg of F133 resin, and 262 mg of 0.085 M trehalose in water, after which it is dispensed on carbon traces, as described in Example 3, for testing. The electrodes are tested for the reduction of hydrogen peroxide at 100 mV.

| Microperoxidase | Current (nA) |
| --- | --- |
| Iron (untreated) | −800 |
| Nickel | −560 |
| Zinc | −190 |
| Copper | −20 |

These results show that microperoxidase can be modified by insertion of a different metal ion and used in a sensor to detect peroxide.

EXAMPLE 10

Demonstration of Detection of Analyte (Glutamate)

The layer containing a peroxidase, e. g., microperoxidase, coupled to carbon can be used for the detection of a peroxide, e. g., hydrogen peroxide. Over the layer containing a peroxidase coupled to carbon can be a layer that contains a biological component, e. g., an enzyme, that reacts with an analyte in a sample to produce a peroxide. In this way the layer containing a peroxidase coupled to carbon is useful for the detection of analytes other than hydrogen peroxide. The following example describes the construction and use of a sensor containing microperoxidase coupled to carbon that can detect glutamate in a sample.

a. Aminated silica was prepared according to the following procedure. 3-Aminotriethoxysilane (TES) (2 g, Sigma Chemical, St. Louis, Mo.) was dispensed into a centrifuge tube (50 mL). Water (8 g) was added. Fumed silica (1 g, Sigma Chemical, St. Louis, Mo.) was added to the centrifuge tube and the solution was rotated about an axis of the tube to disperse the silica. HCl (1 mL, 6N) was added to the centrifuge tube and the resulting solution was rotated about an axis of the tube. The centrifuge tube was then placed in a water bath (70° C.) for one hour. After one hour in the water bath, the TES-silica was washed by (1) centrifuging the solution, thereby creating a pellet of TES-silica, (2) decanting the liquid, (3) adding water (10 mL), and (4) rotating the solution about an axis of the tube to disperse the TES-silica. The washing procedure was repeated three times.

b. Glutamate oxidase enzyme (GLOX) (Yamasa Shoyu Co., Ltd., Japan) was derivatized with 1,2,4,5 benzene tetracarboxylate dianhydride (PMA) (Aldrich, Milwaukee, Wis.) by the following procedure. Glutamate oxidase powder (550 mg) was weighed into a vial. PESK 7.5 (3 mL) was added to dissolve the powder. PMA (15 mg) was then added. The solution was stirred and allowed to react for 30 minutes at room temperature. After reacting, the solution was run through a Sephadex G25 column (Pierce, Rockford, Ill.) with MES buffer, pH 5.5. The brown colored fraction, which contained the PMA derivatized glutamate oxidase, was collected.

c. The PMA-GLOX from Example 10b. was coupled to the aminated silica from Example 10a. by the following procedure. The TES-silica was suspended in water (10 mL) by rotating the centrifuge tube about an axis. Half of the solution was transferred to a clean centrifuge tube (50 ml), thereby removing half of the TES-silica. The PMA-GLOX was then added to the TES-silica that was placed in the clean centrifuge tube. MES buffer, pH 5.5 was added to bring the volume in the centrifuge tube up to a total of 20 mL. 1-Ethyl-3-(3-dimethyl amino propyl) carbodiimide (EDC) (60 mg, Sigma Chemical, St. Louis, Mo.) was added and the solution was mixed. The reaction was allowed to proceed for 60 minutes while agitated. The product was washed by (1) centrifuging the solution, thereby creating a pellet of PMA-GLOX-TES-silica, (2) decanting the liquid, (3) adding water (10 mL), and (4) rotating the solution about an axis of the tube to disperse the PMA-GLOX-TES-silica. The washing procedure was repeated three times.

d. The PMA-GLOX-TES-silica was used to make a paint according to the procedure described in Example 2. The paint formulation consisted of F133 Resin (160 mg), PMA-GLOX-TES-silica (300 mg), and 0.085 M trehalose (690 mg) in water. F133 Resin was described in Example 2. The paint (0.6 $\mu$L) was dispensed over the electrodes that had been previously coated with a microperoxidase paint. The electrodes and their construction were described in Example 3. The microperoxidase paint was formed from a native carbon as described in Example 1. The formulation of the microperoxidase paint was described in Example 2.

e. Ascorbate oxidase (ASOX) was attached to TES-silica using the following procedure. ASOX (62.5 mg) was weighed into a small vial. The enzyme was dissolved in MES pH 5.5 (500 microliters). The resulting solution was added to a Presto Desalting Column (Pierce, Rockford, Ill.) that had been conditioned with MES buffer, pH 5.5. Approximately 3 mL of eluent containing the enzyme was collected from the column. The TES-silica solution as prepared in Example 10a. was centrifuged to create a pellet of TES-silica. The TES-silica pellet (500 mg) was added to the ASOX solution. The solution was rotated about an axis of the tube to mix the ASOX and TES-silica. EDC (5 mg) was added to the mixture and the reaction was allowed to proceed for one hour while agitated. The product was washed by (1) centrifuging the solution, thereby creating a pellet of ASOX-TES-silica, (2) decanting the liquid, (3) adding water (10 mL), and (4) rotating the solution about an axis of the tube to disperse the ASOX-TES-silica. The washing procedure was repeated three times.

f. The ASOX-TES-silica was used to make a paint using the procedure described in Example 2. The paint formula consisted of F133 Resin (130 mg), ASOX-TES-silica (220 mg), and 0.5 M trehalose (775 mg) in water. The paint (0.6 $\mu$L) was dispensed over the PMA-GLOX-TES-silica layer covering the electrodes prepared in Example 10d. F133 Resin was described in Example 2.

g. The electrodes as prepared in Example 10f consisted of a carbon conducting layer, which layer was covered with a layer containing microperoxidase coupled to carbon, which layer was covered with a PMA-GLOX-TES-silica layer, which layer was covered with an ASOX-TES-silica layer. The purpose of the ASOX-TES-silica layer was to react with any ascorbate in the sample. Because ascorbate will react with carbon and create an interfering signal, it is necessary to destroy the ascorbate by reaction with ascorbate oxidase. Unlike most oxidase enzymes, ascorbate oxidase does not produce hydrogen peroxide, so no interfering substance is formed by the enzyme's reaction with ascorbate. The PMA-GLOX-TES-silica layer reacted with glutamate to form hydrogen peroxide. The hydrogen peroxide then reacted with the microperoxidase in the microperoxidase layer. This created a measurable electrical current, which was proportional to the amount of glutamate in the sample, as shown in the following table.

The following currents were measured with solutions of glutamate in PESK 7.5 buffer using the test conditions described in Example 4.

| Glutamate concentration (micromolar) | Current (nanoamps) |
| --- | --- |
| 125 | −188.5 |
| 250 | −362.3 |
| 500 | −682.4 |

The data shows a nearly linear response for the detection of glutamate.

All of the references cited in this application are incorporated by reference.

The present invention has been described with reference to preferred embodiments. One of skill in the art will readily appreciate that changes, alterations or modifications can be made to these embodiments without departing from the true scope and spirit of the invention.

We claim:

1. A multiple-layer article comprising
   (a) an electrode for the determination of an analyte in a sample comprising: a conjugate confined to an electrically conductive surface, said conjugate formed from fine particles of carbon covalently linked to peroxidase, said fine particles of carbon selected from the group consisting of native carbon, derivatized carbon, and carbon-containing conductive compounds, wherein the conjugate of carbon and peroxidase is confined in a resin matrix, and
   (b) at least partially overlying said electrode, a layer comprising a biological component that is capable of reacting with an analyte to produce a peroxide.

2. The article of claim 1 wherein the carbon is native carbon.

3. The article of claim 1 wherein the peroxidase is microperoxidase.

4. The article of claim 1 wherein the biological component is a protein.

5. The article of claim 1 wherein the biological component is an enzyme.

6. The article of claim 1 wherein the peroxide is hydrogen peroxide.

7. The article of claim 1 wherein the carbon is derivatized carbon that has been derivatized with a bifunctional reagent.

8. The article of claim 1 wherein the biological component is contained in a resinous matrix.

9. A method of measuring an analyte of interest in a test sample, said method comprising the steps of
   (1) contacting the sample with a multiple-layer article comprising
      (a) an electrode for the determination of an analyte in a sample comprising: fine particles of carbon selected from the group consisting of native carbon, derivatized carbon, and carbon-containing conductive compounds, said fine particles of carbon covalently linked to peroxidase to form a conjugate, said conjugate confined to an electrically conductive surface, wherein the conjugate of carbon and peroxidase is confined in a resin matrix and
      (b) at least partially overlying said electrode, a layer comprising a biological component that is capable of reacting with an analyte to produce a peroxide, and
   (2) detecting change in electrical signal as a quantitative or qualitative measure of the amount of analyte in the sample.

10. The method of claim 9 wherein the carbon is native carbon.

11. The method of claim 9 wherein the peroxidase is microperoxidase.

12. The method of claim 9 wherein the analyte is glucose or glutamate.

13. The method of claim 9 wherein the biological component is a protein.

14. The method of claim 9 wherein the biological component is an enzyme.

15. The method of claim 9 wherein the peroxide is hydrogen peroxide.

16. The method of claim 9 wherein the carbon is derivatized carbon that has been derivatized with a bifunctional reagent.

17. The method of claim 9 wherein the biological component is contained in a resinous matrix.

* * * * *